United States Patent
Saito et al.

(10) Patent No.: US 10,037,882 B2
(45) Date of Patent: Jul. 31, 2018

(54) METHOD FOR CLEANING WAFER

(71) Applicant: CENTRAL GLASS COMPANY, LIMITED, Yamaguchi (JP)

(72) Inventors: Masanori Saito, Mie (JP); Takashi Saio, Mie (JP); Soichi Kumon, Mie (JP); Shinobu Arata, Mie (JP)

(73) Assignee: CENTRAL GLASS COMPANY, LIMITED, Yamaguchi (JP)

( * ) Notice: Subject to any disclaimer, the term of this patent is extended or adjusted under 35 U.S.C. 154(b) by 129 days.

(21) Appl. No.: 15/026,722

(22) PCT Filed: Sep. 8, 2014

(86) PCT No.: PCT/JP2014/073660
§ 371 (c)(1),
(2) Date: Apr. 1, 2016

(87) PCT Pub. No.: WO2015/049956
PCT Pub. Date: Apr. 9, 2015

(65) Prior Publication Data
US 2016/0254140 A1 Sep. 1, 2016

(30) Foreign Application Priority Data
Oct. 4, 2013 (JP) .................................. 2013-209535

(51) Int. Cl.
*B08B 9/00* (2006.01)
*H01L 21/02* (2006.01)
(Continued)

(52) U.S. Cl.
CPC .......... *H01L 21/02068* (2013.01); *B08B 3/08* (2013.01); *C07F 9/3808* (2013.01);
(Continued)

(58) Field of Classification Search
None
See application file for complete search history.

(56) References Cited

U.S. PATENT DOCUMENTS

| 2012/0164818 A1 | 6/2012 | Kumon et al. |
| 2012/0174945 A1 | 7/2012 | Saio et al. |

(Continued)

FOREIGN PATENT DOCUMENTS

| CN | 102971835 | 3/2013 |
| CN | 103283004 | 9/2013 |

(Continued)

OTHER PUBLICATIONS

EPO machine translation of JP2012033890 (Year: 2018).*
International Search Report dated Oct. 14, 2014, in International (PCT) Application No. PCT/JP2014/073660.

*Primary Examiner* — Eric W Golightly
(74) *Attorney, Agent, or Firm* — Wenderoth, Lind & Ponack, L.L.P.

(57) ABSTRACT

A method for cleaning a wafer that has a pattern of recessed and projected portions formed on a surface thereof and contains at least one element selected from titanium, tungsten, aluminum, copper, tin, tantalum, and ruthenium on a surface of a recessed portion of the pattern. The method at least includes a pre-treating step of holding a cleaning liquid at least in the recessed portion of the pattern; a protective film forming step of holding a protective film forming chemical liquid, which is a chemical liquid containing a water-repellant protective film forming agent, at least in the recessed portion of the pattern after the pre-treating step; and a drying step of removing the liquids from the pattern by drying. The cleaning liquid is acidic if the protective film forming chemical liquid is basic, or is basic if the protective film forming chemical liquid is acidic.

8 Claims, 2 Drawing Sheets

(51) Int. Cl.
  *C07F 9/38*   (2006.01)
  *C11D 7/06*   (2006.01)
  *C11D 7/08*   (2006.01)
  *C11D 7/26*   (2006.01)
  *C11D 7/32*   (2006.01)
  *C11D 11/00*  (2006.01)
  *B08B 3/08*   (2006.01)

(52) U.S. Cl.
  CPC .................. *C11D 7/06* (2013.01); *C11D 7/08* (2013.01); *C11D 7/261* (2013.01); *C11D 7/265* (2013.01); *C11D 7/3209* (2013.01); *C11D 7/3218* (2013.01); *C11D 11/0047* (2013.01)

(56)         References Cited

U.S. PATENT DOCUMENTS

| | | |
|---|---|---|
| 2012/0211025 A1 | 8/2012 | Kumon et al. |
| 2013/0104931 A1 | 5/2013 | Arata et al. |

FOREIGN PATENT DOCUMENTS

| | | |
|---|---|---|
| JP | 4403202 | 1/2010 |
| JP | 4743340 | 8/2011 |
| JP | 2012-33890 | 2/2012 |
| JP | 2012-033890 | 2/2012 |
| JP | 2013-102109 | 5/2013 |
| JP | 2013-118347 | 6/2013 |
| TW | 201232196 | 8/2012 |
| WO | 2012/096133 | 7/2012 |

\* cited by examiner

FIG.1 PRIOR ART
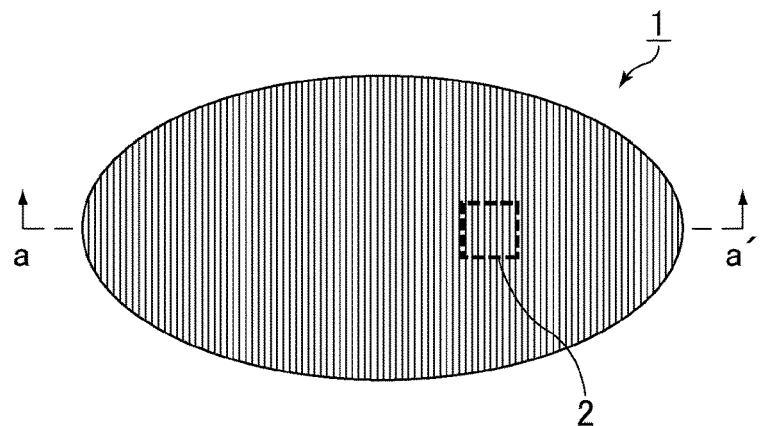
FIG.2 PRIORT ART
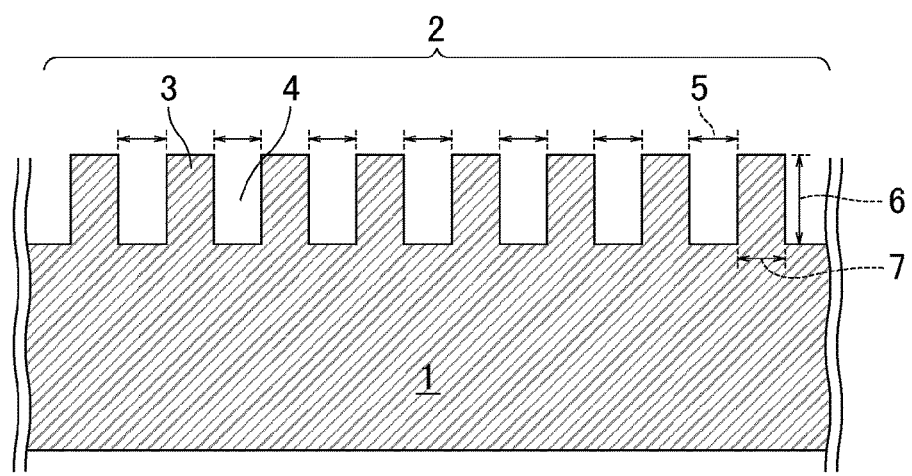
FIG.3
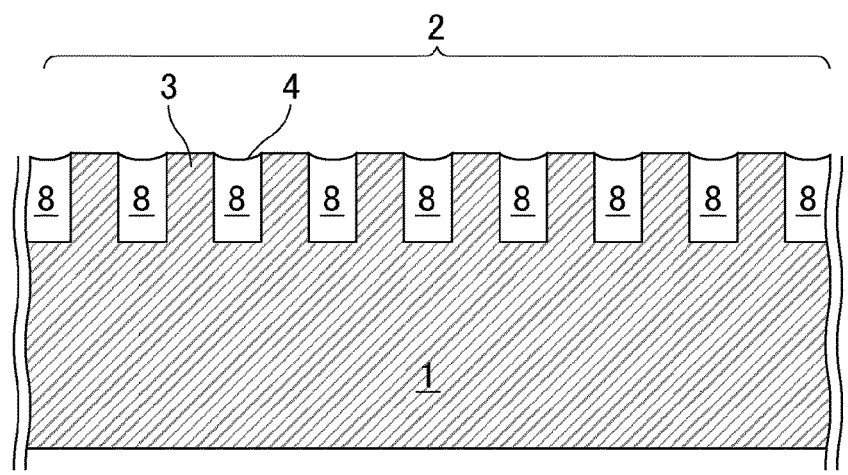

METHOD FOR CLEANING WAFER

TECHNICAL FIELD

The present invention relates to methods for cleaning wafers, for example, a method for cleaning a substrate (wafer) in production of semiconductor devices.

BACKGROUND ART

Semiconductor devices for networks and digital home appliances are required to achieve higher performance and higher functionality, as well as lower power consumption. This leads to miniaturization of circuit patterns, and in response to the progress of such miniaturization, pattern collapse of the circuit patterns becomes a problem. In production of semiconductor devices, cleaning steps are performed many times in order to remove particles and metallic impurities. As a result, the cleaning steps occupy about 30 to 40 percent of the whole process of producing semiconductors. If the aspect ratio of a pattern becomes high as a result of the miniaturization of semiconductor devices, the pattern is collapsed when the air-liquid interface passes through the pattern after cleaning or rinsing in such cleaning steps. This phenomenon is the pattern collapse. In order to prevent occurrence of the pattern collapse, the patterning design needs to be changed. Further, the pattern collapse may cause a reduction in the yield in production. Thus, methods for preventing the pattern collapse in cleaning steps have been desired.

One known effective method of preventing the pattern collapse is formation of a water-repellent protective film on the pattern surface. This water-repellent protective film needs to be formed without drying the pattern surface. Thus, the water-repellent protective film is formed from a water-repellent protective film forming chemical liquid that can impart the water repellency to the pattern surface.

For example, Patent Literature 1 discloses a cleaning technique in which the surface of a wafer having a pattern of recessed and projected portions formed from a silicon-containing film is modified by oxidation, for example, and then a water-repellent protective film is formed on the surface using a water-soluble surfactant or a silane-coupling agent, so that the pattern collapse is prevented.

Patent Literature 2 discloses a cleaning technique in which a water-repellent protective film is formed using a chemical liquid containing any of alkyl amines and alkyl isocyanates on the surface of a wafer having a pattern of recessed and projected portions formed on the surface thereof from a metallic element, so that the pattern collapse is prevented.

Patent Literature 3 discloses a cleaning technique in which a water-repellent protective film is formed using a chemical liquid containing an alkyl phosphonate on the surface of a wafer having a pattern of recessed and projected portions formed on the surface thereof from a metallic element, so that the pattern collapse is prevented.

CITATION LIST

Patent Literature

Patent Literature 1: JP 4403202 B
Patent Literature 2: JP 4743340 B
Patent Literature 3: JP 2013-102109 A

SUMMARY OF INVENTION

Technical Problem

The present invention relates to a technique of cleaning a substrate (wafer) for the purpose of improving the production yield of devices having a fine circuit pattern with a high aspect ratio in production of semiconductor devices, for example. In particular, the present invention relates to a cleaning method for improving a cleaning step that easily causes the pattern collapse on a wafer having a pattern of recessed and projected portions on a surface thereof.

Wafers usually used contain silicon elements on their surfaces. As the pattern is diversified, however, wafers containing any other elements (hereinafter, also referred to as "metallic elements"), such as titanium, tungsten, aluminum, copper, tin, tantalum, and ruthenium, on the surfaces thereof have started to be used. In the case of a wafer containing a substance that insufficiently has a reactive functional group, such as a silanol group, on a surface thereof (e.g., a wafer containing a metallic element on a surface thereof), even the treating liquid disclosed in Patent Literature 1 fails to sufficiently form a water-repellent protective film for preventing the pattern collapse. Therefore, the pattern collapse is not prevented. In contrast, the chemical liquids disclosed in Patent Literature documents 2 and 3 each can actually form a water-repellent protective film on a surface of a wafer containing a metallic element. Still, the water repellency imparted to the wafer surface needs to be improved.

The present invention is devised in order to solve the above disadvantages, and aims to provide a method for cleaning a wafer for the purpose of improving a cleaning step that easily causes the pattern collapse on a wafer (hereinafter, also referred to as a "metallic wafer" or simply a "wafer") having a pattern of recessed and projected portions formed on a surface thereof and containing a metallic element, such as titanium, on a surface of a recessed portion of the pattern.

Solution to Problem

In order to achieve the above purpose, the method for cleaning a wafer of the present invention is a method for cleaning a wafer that has a pattern of recessed and projected portions formed on a surface thereof and contains at least one element selected from titanium, tungsten, aluminum, copper, tin, tantalum, and ruthenium on a surface of a recessed portion of the pattern, the method at least including:

a pre-treating step of holding a cleaning liquid at least in the recessed portion of the pattern;

a protective film forming step of holding a protective film forming chemical liquid at least in the recessed portion of the pattern after the pre-treating step; and a drying step of removing the liquids from the pattern by drying, the protective film forming chemical liquid being a chemical liquid containing a water-repellent protective film forming agent for forming a water-repellent protective film at least on the surface of the recessed portion, the cleaning liquid being acidic if the protective film forming chemical liquid is basic, or being basic if the protective film forming chemical liquid is acidic.

In the production of metallic wafers, cleaning is performed using various cleaning liquids so as to remove particles and metallic impurities before the protective film forming step. In the present invention, the present inventors have found that the water repellency of the wafer surface can be improved by changing the cleaning liquid used in the cleaning before the protective film forming step in accordance with whether the protective film forming chemical liquid (hereinafter, also simply referred to as a "chemical liquid") is acidic or basic. Specifically, the present inventors have found that use of an acidic cleaning liquid if the protective film forming chemical liquid is basic or use of a basic cleaning liquid if the protective film forming chemical liquid is acidic causes the protective film formed on the wafer surface to have a greater contact angle with water, so that the wafer surface has excellent water repellency.

The aforementioned pattern collapse occurs when the air-liquid interface passes through the pattern during drying after cleaning the wafer with a cleaning liquid. In the present invention, the protective film formed on the wafer surface has a great contact angle with water, and thus the wafer surface has improved water repellency. This therefore presumably results in a good tendency of less causing the pattern collapse.

The wafer having a pattern of recessed and projected portions on a surface thereof in the present invention means a wafer with a pattern of recessed and projected portions being formed on a surface thereof by etching, imprinting, or the like technique. Even if the above wafer is provided with other components such as metal conductive lines, it can be a target of the present invention as long as the wafer has a pattern of recessed and projected portions on a surface thereof.

In the present invention, the protective film forming chemical liquid substitutes for the cleaning liquid in the cleaning step for a metallic wafer. This chemical liquid may be replaced by another cleaning liquid.

As mentioned above, the protective film is formed at least on the surface of the recessed portion of the pattern while the protective film forming chemical liquid that has replaced the cleaning liquid after the cleaning step is held at least in the recessed portion of the pattern. In the present invention, the protective film is not necessarily formed in a continuous manner and is not necessarily formed in a uniform manner. Still, in order to impart better water repellency, the protective film is more preferably formed in a continuous and uniform manner.

In the present invention, the protective film is a film that is formed on a wafer surface to decrease the wettability of the wafer surface, in other words, to impart the water repellency. In the present invention, the water repellency means that the surface energy of a surface of an article is reduced and the interaction, such as hydrogen bond or intermolecular force, between water or any other liquid and the surface of the article (at the interface therebetween) is weakened. In particular, the protective film has a higher effect of reducing the interaction with water. Still, the protective film has an effect of reducing the interaction with a liquid mixture of water and a liquid other than water or with a liquid other than water. Such a reduction in the interaction leads to an increase in the contact angle with the liquid on the surface of the article.

In the method for cleaning a wafer of the present invention, when the protective film forming chemical liquid is basic and the cleaning liquid is acidic, the water-repellent protective film forming agent contained in the protective film forming chemical liquid is preferably at least one selected from the group consisting of compounds represented by the following formula [1] and salt compounds thereof:

$$R^1R^2R^3N \qquad [1]$$

wherein $R^1$ is a monovalent organic group having a C1-C18 hydrocarbon group or a monovalent organic group having a C1-C8 fluoroalkyl chain; $R^2$ is a hydrogen atom, a monovalent organic group having a C1-C18 hydrocarbon group, or a monovalent organic group having a C1-C8 fluoroalkyl chain; and $R^3$ is a hydrogen atom, a monovalent organic group having a C1-C18 hydrocarbon group, or a monovalent organic group having a C1-C8 fluoroalkyl chain.

When the basic protective film forming chemical liquid contains at least one selected from the group consisting of the compounds represented by the formula [1] and salt compounds thereof, the wafer preferably at least contains a tungsten element on the surface of the recessed portion of the pattern.

When the protective film forming chemical liquid is acidic and the cleaning liquid is basic in the method for cleaning a wafer of the present invention, the water-repellent protective film forming agent contained in the protective film forming chemical liquid is preferably at least one selected from the group consisting of compounds represented by the following formula [2]:

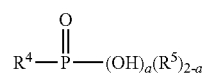

wherein $R^4$ is a C1-C18 monovalent hydrocarbon group in which part or all of the hydrogen atoms may each optionally be replaced by a fluorine atom; $R^5$s are each individually a monovalent organic group having a C1-C18 hydrocarbon group in which part or all of the hydrogen atoms may each optionally be replaced by a fluorine atom; and a is an integer of 0 to 2.

When the acidic protective film forming chemical liquid contains at least one selected from the group consisting of the compounds represented by the formula [2], the wafer preferably at least contains a titanium element on the surface of the recessed portion of the pattern.

The method for cleaning a wafer of the present invention preferably further includes a film removing step of removing the protective film.

The method for producing a wafer of the present invention includes the aforementioned method for cleaning a wafer of the present invention.

Advantageous Effects of Invention

In the method for cleaning a wafer of the present invention, a protective film formed from the protective film forming chemical liquid is excellent in water repellency, and thus shows an effect of preventing the pattern collapse of a metallic wafer. With this method, the step of cleaning a wafer that has a pattern of recessed and projected portions on a surface thereof is improved without decreasing the throughput. Thus, the method can produce a wafer having a pattern of recessed and projected portions at high efficiency.

The method for cleaning a wafer of the present invention can cope with a pattern of recessed and projected portions having an aspect ratio that is expected to more and more increase, for example, up to 7 or higher. Thus, the method leads to a decrease in the cost of producing higher density semiconductor devices. In addition, the method can achieve such progresses without any significant modification of conventional devices. As a result, the method can be applicable to production of a variety of semiconductor devices.

BRIEF DESCRIPTION OF THE DRAWINGS

FIG. 1 is a schematic perspective view of a wafer 1 that has a pattern 2 of recessed and projected portions on a surface thereof.

FIG. 2 is a schematic view of a part of a cross section of the wafer taken along the a-a' line shown in FIG. 1.

FIG. 3 is a schematic view of recessed portions 4 with a protective film forming chemical liquid 8 being held therein in the protective film forming step.

DESCRIPTION OF EMBODIMENTS

Figure 4:
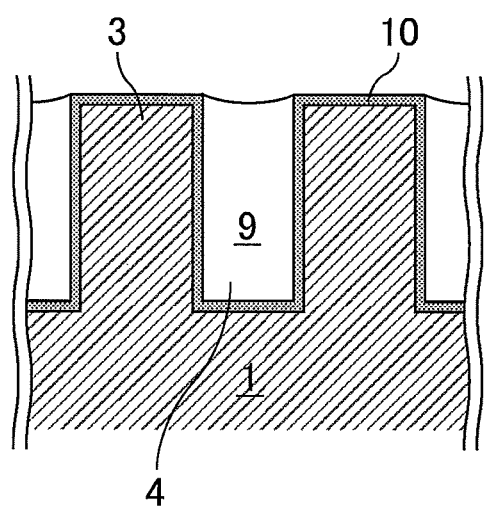
FIG. 4 is a schematic view of the recessed portions 4 with a protective film being formed thereon and a liquid being held therein.

The following will specifically describe embodiments of the present invention. The present invention is not limited to the following embodiments and may be appropriately modified without departing from the spirit of the present invention.

The method for cleaning a wafer of the present invention is a method for cleaning a wafer that has a pattern of recessed and projected portions formed on a surface thereof and contains at least one element selected from titanium, tungsten, aluminum, copper, tin, tantalum, and ruthenium on a surface of a recessed portion of the pattern, the method at least including:

a pre-treating step of holding a cleaning liquid at least in the recessed portion of the pattern;

a protective film forming step of holding a protective film forming chemical liquid at least in the recessed portion of the pattern after the pre-treating step; and a drying step of removing the liquids from the pattern by drying, the protective film forming chemical liquid being a chemical liquid containing a water-repellent protective film forming agent for forming a water-repellent protective film at least on the surface of the recessed portion, the cleaning liquid being acidic if the protective film forming chemical liquid is basic, or being basic if the protective film forming chemical liquid is acidic.

Further, the method for producing a wafer of the present invention includes the method for cleaning a wafer of the present invention.

Examples of the metallic wafer include wafers, such as silicon wafers, wafers composed of multiple components including silicon and/or silicon oxide (SiO$_2$), silicon carbide wafers, sapphire wafers, various compound semiconductor wafers, and plastic wafers, whose surfaces are coated with a layer of a substance containing a titanium element (e.g., titanium, titanium nitride, titanium oxide), a substance containing a tungsten element (e.g., tungsten, tungsten oxide), a substance containing an aluminum element (e.g., aluminum, aluminum oxide), a substance containing a copper element (e.g., copper, copper oxide), a substance containing a tin element (e.g., tin, tin oxide), a substance containing a tantalum element (e.g., tantalum nitride, tantalum oxide), or a substance containing a ruthenium element (e.g., ruthenium, ruthenium oxide); and wafers covered with a multilayer film having at least one layer of a substance containing any of the above metallic elements. The following pattern forming step is performed on the layer including the layer of a substance containing any of the above metallic elements. Examples thereof also include those in which, after a pattern of recessed and projected portions is formed, at least part of the surface of the pattern is constituted by a substance having at least one element selected from the above metallic elements.

In the present invention, the following steps are usually performed in many cases before the surface treatment using a protective film forming chemical liquid:

a pattern forming step of giving a pattern of recessed and projected portions to the wafer surface;

a pre-treating step 1 of cleaning the wafer surface using an aqueous cleaning liquid; and a pre-treating step 2 of replacing the aqueous cleaning liquid by a cleaning liquid A that is different from the aqueous cleaning liquid (hereinafter, also simply referred to as a "cleaning liquid A").

Either the pre-treating step 1 or the pre-treating step 2 may be omitted.

In the present invention, the pre-treating step 1, the pre-treating step 2, or both of the steps may be simply referred to as a "pre-treating step(s)".

The method of forming a pattern in the pattern forming step is as follows. First, a resist material is applied to the wafer surface and exposed to light through a resist mask. The exposed portion or non-exposed portion of the resist material is etched and removed, so that a resist having a desired pattern of recessed and projected portions is prepared. Alternatively, the resist having a pattern of recessed and projected portions can be prepared by pressing a patterned mold to the resist material. Next, the wafer is etched. Here, the wafer surface corresponding to the recessed portion of the resist pattern is selectively etched. Finally, the resist is peeled off. Thereby, a wafer having a pattern of recessed and projected portions is obtained.

The pattern forming step provides a wafer having a pattern of recessed and projected portions formed on a surface thereof and containing at least one element selected from titanium, tungsten, aluminum, copper, tin, tantalum, and ruthenium on a surface of a recessed portion of the pattern.

Examples of the aqueous cleaning liquid used in the pre-treating step 1 include water and any aqueous solution (water content: 10% by mass or more, for example) prepared by adding at least one of organic solvents, hydrogen peroxide, ozone, acids, bases, and surfactants to water.

In the pre-treating step 1, the replacement by the aqueous cleaning liquid may be performed twice or more. The aqueous cleaning liquid may be different in each case.

If the surface cleaning with an aqueous cleaning liquid in the pre-treating step 1 is followed by dry-removal of the aqueous cleaning liquid, or by replacement of the aqueous cleaning liquid by water and dry-removal of the water, the collapse of a pattern whose recessed portion has a narrow width and whose projected portion has a high aspect ratio may easily occur. The pattern is defined as illustrated in FIG. 1 and FIG. 2. FIG. 1 is one example of a schematic perspective view of a wafer 1 having a pattern 2 of recessed and projected portions formed on a surface thereof, and FIG. 2 is a schematic view of part of a cross section of the wafer taken along the a-a' line shown in FIG. 1. The width 5 of each recessed portion is defined by the gap between one projected portion 3 and an adjacent projected portion 3, as illustrated in FIG. 2. The aspect ratio of each projected portion is calculated by dividing the height 6 of the projected portion by the width 7 of the projected portion. The pattern collapse may easily occur during the cleaning step when the recessed portion has a width of 70 nm or smaller, especially 45 nm or smaller, and the projected portion has an aspect ratio of 4 or higher, especially 6 or higher.

The cleaning liquid A used in the pre-treating step 2 is an organic solvent, a mixture of the organic solvent and an aqueous cleaning liquid, or a cleaning liquid prepared by mixing any of these liquids with at least one of acids, bases, and surfactants. Further, a step of holding a protective film forming chemical liquid at least in the recessed portion of the pattern is preferably performed by replacing the cleaning liquid A by the protective film forming chemical liquid (protective film forming step).

In the present invention, the wafer may be cleaned by any technique as long as the chemical liquid or the cleaning liquid can be held at least in the recessed portion of the pattern of the wafer. Examples of the technique of cleaning a wafer include single wafer cleaning techniques represented by spin cleaning in which a single wafer is substantially horizontally held and rotated, and a liquid is applied to the rotation center of the wafer and the vicinity thereof so that the wafer is cleaned one by one, and batch techniques in which multiple wafers are immersed in a cleaning tank so that the wafers are collectively cleaned. The chemical liquid and the cleaning liquid may be in any form, such as liquid or steam, when applied at least to the recessed portion of the pattern of the wafer as long as they are in the liquid form when held in the recessed portion.

Examples of the organic solvent that is one preferred example of the cleaning liquid A include hydrocarbons, esters, ethers, ketones, halogen-containing solvents, sulfoxide-type solvents, lactone-type solvents, carbonate-type solvents, alcohols, derivatives of polyhydric alcohols, and nitrogen-containing solvents.

Examples of the hydrocarbons include toluene, benzene, xylene, hexane, heptane, and octane. Examples of the esters include ethyl acetate, propyl acetate, butyl acetate, and ethyl acetoacetate. Examples of the ethers include diethyl ether, dipropyl ether, dibutyl ether, tetrahydrofuran, and dioxane. Examples of the ketones include acetone, acetyl acetone, methyl ethyl ketone, methyl propyl ketone, methyl butyl ketone, and cyclohexanone. Examples of the halogen-containing solvents include perfluorocarbons such as perfluorooctane, perfluorononane, perfluorocyclopentane, perfluorocyclohexane, and hexafluorobenzene, hydrofluorocarbons such as 1,1,1,3,3-pentafluorobutane, octafluorocyclopentane, 2,3-dihydrodecafluoropentane, and ZEORORA H (Zeon Corp.), hydrofluoroethers such as methyl perfluoroisobutyl ether, methyl perfluorobutyl ether, ethyl perfluorobutyl ether, ethyl perfluoroisobutyl ether, ASAHIKLIN AE-3000 (Asahi Glass Co., Ltd.), and Novec 7100, Novec 7200, Novec 7300, and Novec 7600 (each available from 3M), chlorocarbons such as tetrachloromethane, hydrochlorocarbons such as chloroform, chlorofluorocarbons such as dichlorodifluoromethane, hydrochlorofluorocarbons such as 1,1-dichloro-2,2,3,3,3-pentafluoropropane, 1,3-dichloro-1,1,2,2,3-pentafluoropropane, 1-chloro-3,3,3-trifluoropropene, and 1,2-dichloro-3,3,3-trifluoropropene, perfluoroethers, and perfluoropolyethers. Examples of the sulfoxide-type solvents include dimethyl sulfoxide. Examples of the lactone-type solvents include γ-butyrolactone, γ-valerolactone, γ-hexanolactone, γ-heptanolactone, γ-octanolactone, γ-nonanolactone, γ-decanolactone, γ-undecanolactone, γ-dodecanolactone, valerolactone, δ-hexanolactone, δ-octanolactone, δ-nonanolactone, δ-decanolactone, δ-undecanolactone, δ-dodecanolactone, and ε-hexanolactone. Examples of the carbonate-type solvents include dimethyl carbonate, ethyl methyl carbonate, diethyl carbonate, and propylene carbonate. Examples of the alcohols include methanol, ethanol, propanol, butanol, ethylene glycol, diethylene glycol, 1,2-propane diol, 1,3-propane diol, dipropylene glycol, 1,2-butanediol, 1,3-butanediol, 1,4-butanediol, triethylene glycol, tripropylene glycol, tetraethylene glycol, tetrapropylene glycol, and glycerin. Examples of the derivatives of polyhydric alcohols include ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, diethylene glycol monopropyl ether, diethylene glycol monobutyl ether, triethylene glycol monomethyl ether, triethylene glycol monoethyl ether, triethylene glycol monopropyl ether, triethylene glycol monobutyl ether, tetraethylene glycol monomethyl ether, tetraethylene glycol monoethyl ether, tetraethylene glycol monopropyl ether, tetraethylene glycol monobutyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, dipropylene glycol monobutyl ether, tripropylene glycol monomethyl ether, tripropylene glycol monoethyl ether, tripropylene glycol monopropyl ether, tripropylene glycol monobutyl ether, tetrapropylene glycol monomethyl ether, butylene glycol monomethyl ether, ethylene glycol dimethyl ether, ethylene glycol diethyl ether, ethylene glycol dibutyl ether, ethylene glycol monomethyl ether acetate, ethylene glycol monoethyl ether acetate, ethylene glycol monobutyl ether acetate, ethylene glycol diacetate, diethylene glycol dimethyl ether, diethylene glycol ethyl methyl ether, diethylene glycol diethyl ether, diethylene glycol butyl methyl ether, diethylene glycol dibutyl ether, diethylene glycol monomethyl ether acetate, diethylene glycol monoethyl ether acetate, diethylene glycol monobutyl ether acetate, diethylene glycol diacetate, triethylene glycol dimethyl ether, triethylene glycol diethyl ether, triethylene glycol dibutyl ether, triethylene glycol butyl methyl ether, triethylene glycol monomethyl ether acetate, triethylene glycol monoethyl ether acetate, triethylene glycol monobutyl ether acetate, triethylene glycol diacetate, tetraethylene glycol dimethyl ether, tetraethylene glycol diethyl ether, tetraethylene glycol dibutyl ether, tetraethylene glycol monomethyl ether acetate, tetraethylene glycol monoethyl ether acetate, tetraethylene glycol monobutyl ether acetate, tetraethylene glycol diacetate, propylene glycol dimethyl ether, propylene glycol diethyl ether, propylene glycol dibutyl ether, propylene glycol monomethyl ether acetate, propylene glycol monoethyl ether acetate, propylene glycol monobutyl ether acetate, propylene glycol diacetate, dipropylene glycol dimethyl ether, dipropylene glycol methyl propyl ether, dipropylene glycol diethyl ether, dipropylene glycol dibutyl ether, dipropylene glycol monomethyl ether acetate, dipropylene glycol monoethyl ether acetate, dipropylene glycol monobutyl ether acetate, dipropylene glycol diacetate, tripropylene glycol dimethyl ether, tripropylene glycol diethyl ether, tripropylene glycol dibutyl ether, tripropylene glycol monomethyl ether acetate, tripropylene glycol monoethyl ether acetate, tripropylene glycol monobutyl ether acetate, tripropylene glycol diacetate, tetrapropylene glycol dimethyl ether, tetrapropylene glycol monomethyl ether acetate, tetrapropylene glycol diacetate, butylene glycol dimethyl ether, butylene glycol monomethyl ether acetate, butylene glycol diacetate, and glycerin triacetate. Examples of the nitrogen-containing solvents include formamide, N,N-dimethyl formamide, N,N-dimethyl acetamide, N-methyl-2-pyrrolidone, diethyl amine, triethyl amine, and pyridine.

For good cleanliness, the cleaning liquid A is preferably an organic solvent or a liquid mixture of water and an organic solvent. In order to make it easy to replace the aqueous cleaning liquid by the cleaning liquid A, the organic solvent preferably contains a water-soluble organic solvent (solubility: 5 parts by mass or more for 100 parts by mass of water).

In the pre-treating step 2, the replacement by the cleaning liquid A may be performed twice or more. In other words, after the aqueous cleaning liquid used in the pre-treating step 1 is replaced by a first cleaning liquid A, this first cleaning liquid A may be successively replaced by different multiple cleaning liquids A one after another, and finally the last cleaning liquid A may be replaced by the protective film forming chemical liquid.

If the aqueous cleaning liquid used in the pre-treating step 1 is directly replaceable by the protective film forming chemical liquid, the replacement by the cleaning liquid A (the pre-treating step 2) may be omitted.

In the present invention, an acidic cleaning liquid is used in the pre-treating step if the protective film forming chemical liquid to be mentioned later is basic, or a basic cleaning liquid is used in the pre-treating step if the protective film forming chemical liquid is acidic.

Examples of (1) the cases of using a basic chemical liquid include: (1-1) a case of using an acidic cleaning liquid in one of the pre-treating step 1 and the pre-treating step 2 but using a non-basic cleaning liquid in the other step; (1-2) a case of using a basic cleaning liquid in the pre-treating step 1 and using an acidic cleaning liquid in the pre-treating step 2; (1-3) a case of using an acidic cleaning liquid in both the pre-treating step 1 and the pre-treating step 2; and (1-4) a case of using an acidic cleaning liquid in the pre-treating step 1 and omitting the pre-treating step 2.

Similarly, examples of (2) the cases of using an acidic chemical liquid include: (2-1) a case of using a basic cleaning liquid in one of the pre-treating step 1 and the pre-treating step 2 but using a non-acidic cleaning liquid in the other step; (2-2) a case of using an acidic cleaning liquid in the pre-treating step 1 and using a basic cleaning liquid in the pre-treating step 2; (2-3) a case of using a basic cleaning liquid in both the pre-treating step 1 and the pre-treating step 2; and (2-4) a case of using a basic cleaning liquid in the pre-treating step 1 and omitting the pre-treating step 2.

The acid contained in the acidic cleaning liquid may be an inorganic acid or may be an organic acid.

Examples of the inorganic acid include hydrochloric acid, nitric acid, sulfuric acid, hydrofluoric acid, and phosphoric acid.

Examples of the organic acid include acetic acid, propionic acid, butanoic acid, pentanoic acid, hexanoic acid, heptanoic acid, octanoic acid, nonanoic acid, decanoic acid, oxalic acid, maleic acid, benzoic acid, formic acid, malonic acid, sulfonic acid, phthalic acid, fumaric acid, citric acid, tartaric acid, trifluoroacetic acid, trifluoroacetic anhydride, pentafluoropropionic acid, and pentafluoropropionic anhydride.

In order to achieve better water repellency, the acidic cleaning liquid preferably has a pH of 5 or less, more preferably 3 or less.

The acidic cleaning liquid may be held for any period of time. For good productivity, the holding time is preferably 1 second to 10 minutes, more preferably 1 second to 3 minutes. If the acidic cleaning liquid is held in multiple batches, the above holding time is the sum of the time periods of holding the acidic cleaning liquid.

The base contained in the basic cleaning liquid may be an inorganic base or may be an organic base.

Examples of the inorganic base include sodium hydroxide, potassium hydroxide, barium hydroxide, calcium hydroxide, and ammonia.

Examples of the organic base include pyridine, trimethylamine, triethylamine, monoethanolamine, diethanolamine, dimethyl monoethanolamine, monomethyl diethanolamine, triethanolamine, 2-hydroxyethyltrimethylammonium hydroxide (choline), and tetramethylammonium hydroxide.

In order to achieve better water repellency, the basic cleaning liquid preferably has a pH of 9 or greater, more preferably 11 or greater.

The basic cleaning liquid may be held for any period of time. For good productivity, the holding time is preferably 1 second to 10 minutes, more preferably 1 second to 3 minutes. If the basic cleaning liquid is held in multiple batches, the above holding time is the sum of the time periods of holding the basic cleaning liquid.

FIG. 3 is a schematic view of the recessed portions 4 with a protective film forming chemical liquid 8 being held therein in the protective film forming step. The wafer illustrated in the schematic view of FIG. 3 is a part of the cross section taken along the a-a' line shown in FIG. 1. At this time, a protective film is formed on the surface of the recessed portions 4, so that the water repellency is imparted to the surface.

The portion where the protective film can be formed from the chemical liquid is the surface of a portion of a substance containing at least one element selected from the above metallic elements in the pattern. Thus, the protective film may be formed at least on part of the surface of the recessed portions of the metallic wafer. For wafers composed of multiple components including a substance containing at least one element selected from the above metallic elements, the protective film can be formed on the surface of the substance containing at least one element selected from the above metallic elements. The wafers composed of multiple components include those in which a substance containing at least one element selected from the metallic elements forms at least part of the surface of the recessed portions and those in which, after a pattern of recessed and projected portions is formed, at least part of the surface of the recessed portion is composed of a substance containing at least one element selected from the metallic elements.

The protective film forming chemical liquid is a chemical liquid for forming a protective film at least on the surface of the recessed portion after the metallic wafer cleaning step and before the drying step, and contains a protective film forming agent and a solvent.

When the protective film forming chemical liquid is basic, the water-repellent protective film forming agent contained in the protective film forming chemical liquid is preferably at least one selected from the group consisting of compounds represented by the following formula [1] and salt compounds thereof:

$$R^1R^2R^3N \qquad [1]$$

wherein $R^1$ is a monovalent organic group having a C1-C18 hydrocarbon group or a monovalent organic group having a C1-C8 fluoroalkyl chain; $R^2$ is a hydrogen atom, a monovalent organic group having a C1-C18 hydrocarbon group, or a monovalent organic group having a C1-C8 fluoroalkyl chain; $R^3$ is a hydrogen atom, a monovalent organic group having a C1-C18 hydrocarbon group, or a monovalent organic group having a C1-C8 fluoroalkyl chain.

Examples of the compounds represented by the formula [1] and the salt compounds thereof include compounds such as $C_5H_{11}NH_2$, $C_6H_{13}NH_2$, $C_7H_{15}NH_2$, $C_8H_{17}NH_2$, $C_9H_{19}NH_2$, $C_{10}H_{21}NH_2$, $C_{11}H_{23}NH_2$, $C_{12}H_{25}NH_2$, $C_{13}H_{27}NH_2$, $C_{14}H_{29}NH_2$, $C_{15}H_{31}NH_2$, $C_{16}H_{33}NH_2$, $C_{17}H_{35}NH_2$, $C_{18}H_{37}NH_2$, $CF_3NH_2$, $C_2F_5NH_2$, $C_3F_7NH_2$, $C_4F_9NH_2$, $C_5F_{11}NH_2$, $C_6F_{13}NH_2$, $C_7F_{15}NH_2$, $C_8F_{17}NH_2$, $C_4Cl_9NH_2$, $C_5Cl_{11}NH_2$, $C_6Cl_{13}NH_2$, $C_7Cl_{15}NH_2$, $C_8Cl_{17}NH_2$, $C_4Br_9NH_2$, $C_5Br_{11}NH_2$, $C_6Br_{13}NH_2$, $C_7Br_{15}NH_2$, $C_8Br_{17}NH_2$, $C_4I_9NH_2$, $C_5I_{11}NH_2$, $C_6I_{13}NH_2$, $C_7I_{15}NH_2$, $C_8I_7NH_2$, $C_4F_7H_2NH_2$, $C_6F_{11}H_2NH_2$, $C_8F_{15}H_2NH_2$, $C_4Cl_7H_2NH_2$, $C_6Cl_{11}H_2NH_2$, $C_8Cl_{15}H_2NH_2$, $C_4Br_7H_2NH_2$, $C_6Br_{11}H_2NH_2$, $C_8Br_{15}H_2NH_2$, $C_4I_7H_2NH_2$, $C_6I_{11}H_2NH_2$, $C_8I_{15}H_2NH_2$, $C_4F_7Cl_2NH_2$, $C_4F_7Br_2NH_2$, $C_4F_7I_2NH_2$, $(C_3H_7)_2NH$, $(C_4H_9)_2NH$, $(C_5H_{11})_2NH$, $(C_6H_{13})_2 NH$, $(C_7H_{15})_2NH$, $(C_8H_{17})_2NH$, $(C_9H_{19})_2NH$, $(C_{10}H_{21})_2 NH$, $(C_{11}H_{23})_2NH$, $(C_{12}H_{25})_2NH$, $(C_{13}H_{27})_2NH$, $(C_{14}H_{29})_2 NH$, $(C_{15}H_{31})_2NH$, $(C_{16}H_{33})_2NH$, $(C_{17}H_{35})_2NH$, $(C_{18}H_{37})_2 NH$, $(CF_3)_2NH$, $(C_2F_5)_2NH$, $(C_3F_{17})_2NH$, $(C_4F_9)_2NH$, $(C_5F_{11})_2NH$, $(C_6F_{13})_2NH$, $(C_7F_{15})_2NH$, $(C_8F_{17})_2NH$, $(C_4Cl_9)_2NH$, $(C_5Cl_{11})_2NH$, $(C_6Cl_{13})_2NH$, $(C_7Cl_{15})_2NH$, $(C_8Cl_{17})_2NH$, $(C_4Br_9)_2NH$, $(C_5Br_{11})_2NH$, $(C_6Br_{13})_2NH$, $(C_7Br_{15})_2NH$, $(C_8Br_{17})_2NH$, $(C_4I_9)_2NH$, $(C_5I_{11})_2NH$, $(C_6I_{13})_2NH$, $(C_7I_{15})_2NH$, $(C_8I_{17})_2NH$, $(C_4F_7H_2)_2NH$, $(C_6F_{11}H_2)_2NH$, $(C_8F_{15}H_2)_2NH$, $(C_4Cl_7H_2)_2NH$, $(C_6Cl_{11}H_2)_2 NH$, $(C_8Cl_{15}H_2)_2NH$, $(C_4Br_7H_2)_2NH$, $(C_6Br_{11}H_2)_2NH$, $(C_8Br_{15}H_2)_2NH$, $(C_4I_7H_2)_2NH$, $(C_6I_{11}H_2)_2 NH$, $(C_8I_{15}H_2)_2NH$, $(C_4F_7Cl_2)_2NH$, $(C_4F_7Br_2)_2NH$, $(C_4F_7I_2)_2NH$, $(C_2H_5)_3N$, $(C_3H_7)_3N$, $(C_4H_9)_3N$, $(C_5H_{11})_3N$, $(C_6H_{13})_3N$, $(C_7H_{15})_3N$, $(C_8H_{17})_3N$, $(C_9H_{19})_3N$, $(C_{10}H_{21})_3 N$, $(C_{11}H_{23})_3N$, $(C_{12}H_{25})_3N$, $(C_{13}H_{27})_3N$, $(C_{14}H_{29})_3N$, $(C_{15}H_{31})_3N$, $(C_{16}H_{33})_3N$, $(C_{17}H_{35})_3N$, $(C_{18}H_{37})_3N$, $(CF_3)_3 N$, $(C_2F_5)_3N$, $(C_3F_7)_3N$, $(C_4F_9)_3N$, $(C_5F_{11})_3N$, $(C_6F_{13})_3N$, $(C_7F_{15})_3N$, $(C_8F_{17})_3N$, $(C_4Cl_9)_3N$, $(C_5Cl_{11})_3N$, $(C_6Cl_{13})_3N$, $(C_7Cl_{15})_3N$, $(C_8Cl_{17})_3N$, $(C_4Br_9)_3N$, $(C_5Br_{11})_3N$, $(C_6Br_{13})_3 N$, $(C_7Br_{15})_3N$, $(C_8Br_{17})_3N$, $(C_4I_9)_3N$, $(C_5I_{11})_3N$, $(C_6I_{13})_3 N$, $(C_7I_{15})_3N$, $(C_8I_{17})_3N$, $(C_4F_7H_2)_3N$, $(C_6F_{11}H_2)_3N$, $(C_8F_{15}H_2)_3N$, $(C_4Cl_7H_2)_3N$, $(C_6Cl_{11}H_2)_3N$, $(C_8Cl_{15}H_2)_3N$, $(C_4Br_7H_2)_3N$, $(C_6Br_{11}H_2)_3N$, $(C_8Br_{15}H_2)_3N$, $(C_4I_7H_2)_3N$, $(C_6I_{11}H_2)_3N$, $(C_8I_{15}H_2)_3N$, $(C_4F_7Cl_2)_3N$, $(C_4F_7Br_2)_3N$, $(C_4F_7I_2)_3N$, $(C_5H_{11})(CH_3) NH$, $(C_6H_{13})(CH_3) NH$, $(C_7H_{15})(CH_3) NH$, $(C_8H_{17})(CH_3) NH$, $(C_9H_{19})(CH_3) NH$, $(C_{10}H_{21})(CH_3) NH$, $(C_{11}H_{23})(CH_3) NH$, $(C_{12}H_{25})(CH_3) NH$, $(C_{13}H_{27})(CH_3) NH$, $(C_{14}H_{29})(CH_3) NH$, $(C_{15}H_{31})(CH_3) NH$, $(C_{16}H_{33})(CH_3) NH$, $(C_{17}H_{35})(CH_3) NH$, $(C_{18}H_{37})(CH_3) NH$, $(CF_3)(CH_3) NH$, $(C_2F_5)(CH_3) NH$, $(C_3F_7)(CH_3) NH$, $(C_4F_9)(CH_3)NH$, $(C_5F_{11})(CH_3)NH$, $(C_6F_{13})(CH_3) NH$, $(C_7F_{15})(CH_3) NH$, $(C_8F_{17})(CH_3) NH$, $(C_3H_7)(CH_3)_2N$, $(C_4H_9)(CH_3)_2N$, $(C_5H_{11})(CH_3)_2N$, $(C_6H_{13})(CH_3)_2N$, $(C_7H_{15})(CH_3)_2N$, $(C_8H_{17})(CH_3)_2N$, $(C_9H_{19})(CH_3)_2N$, $(C_{10}H_{21})(CH_3)_2N$, $(C_{11}H_{23})(CH_3)_2N$, $(C_{12}H_{25})(CH_3)_2N$, $(C_{13}H_{27})(CH_3)_2N$, $(C_{14}H_{29})(CH_3)_2N$, $(C_{15}H_{31})(CH_3)_2N$, $(C_{16}H_{33})(CH_3)_2N$, $(C_{17}H_{35})(CH_3)_2N$, $(C_{18}H_{37})(CH_3)_2N$, $(CF_3)(CH_3)_2N$, $(C_2F_5)(CH_3)_2N$, $(C_3F_7)(CH_3)_2N$, $(C_4F_9)(CH_3)_2N$, $(C_5F_{11})(CH_3)_2N$, $(C_6F_{13})(CH_3)_2N$, $(C_7F_{15})(CH_3)_2 N$, and $(C_8F_{17})(CH_3)_2N$, inorganic acid salts such as carbonates, hydrochlorides, sulfates, and nitrates thereof, and organic acid salts such as acetates, propionates, butyrates, phthalates, trifluoroacetates, and pentafluoropropionates thereof.

If the water-repellent protective film forming agent forms a salt, the protective film forming chemical liquid may contain the water-repellent protective film forming agent or a salt thereof, or a mixture thereof.

In order to impart better water repellency, the water-repellent protective film forming agent is preferably at least one selected from the group consisting of compounds represented by the formula [1] and salt compounds thereof wherein $R^1$ is a monovalent organic group having a C1-C18 hydrocarbon group, $R^2$ is a hydrogen atom or a monovalent organic group having a C1-C18 hydrocarbon group, and $R^3$ is a hydrogen atom or a monovalent organic group having a C1-C18 hydrocarbon group.

The water-repellent protective film forming agent more preferably has a hydrophobic portion including a linear hydrocarbon group consisting of carbon and hydrogen atoms. If the linear hydrocarbon group at the hydrophobic portion consists of carbon and hydrogen atoms, the hydrophobic portion of the water-repellent protective film forming agent is likely to align in the direction perpendicular to the surface of the resulting protective film, thereby improving the effect of imparting the water repellency. Thus, this configuration is more preferred.

In consideration of the affinity with metallic substances and the effect of imparting the water repellency, particularly preferred examples of the aforementioned water-repellent protective film forming agent include compounds represented by the formula [1], such as $C_6H_{13}NH_2$, $C_7H_{15}NH_2$, $C_8H_{17}NH_2$, $C_9H_{19}NH_2$, $C_{10}H_{21}NH_2$, $C_{11}H_{23}NH_2$, $C_{12}H_{25}NH_2$, $C_{13}H_{27}NH_2$, $C_{14}H_{29}NH_2$, $C_{15}H_{31}NH_2$, $C_{16}H_{33}NH_2$, $C_{17}H_{35}NH_2$, $C_{18}H_{37}NH_2$, $(C_4H_9)_2NH$, $(C_5H_{11})_2 NH$, $(C_6H_{13})_2NH$, $(C_7H_{15})_2NH$, $(C_8H_{17})_2NH$, $(C_9H_{19})_2 NH$, $(C_{10}H_{21})_2NH$, $(C_{11}H_{23})_2NH$, $(C_{12}H_{25})_2NH$, $(C_{13}H_{27})_2 NH$, $(C_{14}H_{29})_2NH$, $(C_{15}H_{31})_2NH$, $(C_{16}H_{33})_2NH$, $(C_{17}H_{35})_2 NH$, $(C_{18}H_{37})_2NH$, $(C_4H_9)_3N$, $(C_5H_{11})_3N$, $(C_6H_{13})_3N$, $(C_7H_{15})_3N$, $(C_8H_{17})_3N$, $(C_9H_{19})_3N$, $(C_{10}H_{21})_3 N$, $(C_{11}H_{23})_3 N$, $(C_{12}H_{25})_3N$, $(C_{13}H_{27})_3N$, $(C_{14}H_{29})_3N$, $(C_{15}H_{31})_3N$, $(C_{16}H_{33})_3N$, $(C_{17}H_{35})_3N$, $(C_{18}H_{37})_3N$, $(C_5H_{11})(CH_3) NH$, $(C_6H_{13})(CH_3)NH$, $(C_7H_{15})(CH_3)NH$, $(C_8H_{17})(CH_3)NH$, $(C_9H_{19})(CH_3)NH$, $(C_{10}H_{21})(CH_3) NH$, $(C_{11}H_{23})(CH_3) NH$, $(C_{12}H_{25})(CH_3) NH$, $(C_{13}H_{27})(CH_3) NH$, $(C_{14}H_{29})(CH_3) NH$, $(C_{15}H_{31})(CH_3) NH$, $(C_{16}H_{33})(CH_3) NH$, $(C_{17}H_{35})(CH_3) NH$, $(C_{18}H_{37})(CH_3)NH$, $(C_4H_9)(CH_3)_2 N$, $(C_5H_{11})(CH_3)_2N$, $(C_6H_{13})(CH_3)_2N$, $(C_7H_{15})(CH_3)_2N$, $(C_8H_{17})(CH_3)_2N$, $(C_9H_{19})(CH_3)_2N$, $(C_{10}H_{21})(CH_3)_2N$, $(C_{11}H_{23})(CH_3)_2N$, $(C_{12}H_{25})(CH_3)_2N$, $(C_{13}H_{27})(CH_3)_2N$, $(C_{14}H_{29})(CH_3)_2N$, $(C_{15}H_{31})(CH_3)_2N$, $(C_{16}H_{33})(CH_3)_2N$, $(C_{17}H_{35})(CH_3)_2N$, and $(C_{18}H_{37})(CH_3)_2N$, inorganic acid salts such as carbonates, hydrochlorides, sulfates, and nitrates thereof, and organic acid salts such as acetates, propionates, butyrates, phthalates, trifluoroacetates, and pentafluoropropionates thereof.

When the basic protective film forming chemical liquid contains at least one selected from the group consisting of the compounds represented by the formula [1] and salt compounds thereof, the chemical liquid is likely to form an excellent water-repellent protective film on the surface of an article containing a tungsten element on the surface thereof. Thus, the wafer preferably at least contains a tungsten element on the surface of the recessed portion of the pattern. The chemical liquid is also likely to form an excellent water-repellent protective film on the surface of an article containing a ruthenium element on the surface thereof. Thus, the wafer may at least contain a ruthenium element on the surface of the recessed portion of the pattern.

When the protective film forming chemical liquid is basic, the water-repellent protective film forming agent contained in the protective film forming chemical liquid may be at least one selected from the group consisting of compounds having a nitrogen-containing cyclic functional group such as an imidazoline ring represented by the following formula and salt compounds thereof.

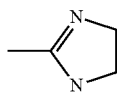

When the protective film forming chemical liquid is acidic, the water-repellent protective film forming agent contained in the protective film forming chemical liquid is preferably at least one selected from the group consisting of compounds represented by the following formula [2]:

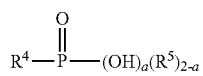

[2]

wherein $R^4$ is a C1-C18 monovalent hydrocarbon group in which part or all of the hydrogen atoms may each optionally be replaced by a fluorine atom; $R^5$s are each individually a monovalent organic group having a C1-C18 hydrocarbon group in which part or all of the hydrogen atoms may each optionally be replaced by a fluorine atom; and a is an integer of 0 to 2.

Examples of the hydrocarbon group in $R^5$ of the formula [2] include alkyl groups and alkylene groups in each of which part or all of the hydrogen atoms may each optionally be replaced by a fluorine atom.

$R^5$ is preferably $-OR^9$ wherein $R^9$ is a C1-C18 hydrocarbon group. In order to impart better water repellency, the carbon number of $R^9$ is preferably 1 to 8, in particular 1 to 4. $R^9$ is preferably a linear alkyl group.

Examples of the compounds represented by the formula [2] include $CH_3P(O)(OH)_2$, $C_2H_5P(O)(OH)_2$, $C_3H_7P(O)(OH)_2$, $C_4H_9P(O)(OH)_2$, $C_5H_{11}P(O)(OH)_2$, $C_6H_{13}P(O)(OH)_2$, $C_7H_{15}P(O)(OH)_2$, $C_8H_{17}P(O)(OH)_2$, $C_9H_{19}P(O)(OH)_2$, $C_{10}H_{21}P(O)(OH)_2$, $C_{11}H_{23}P(O)(OH)_2$, $C_{12}H_{25}P(O)(OH)_2$, $C_{13}H_{27}P(O)(OH)_2$, $C_{14}H_{29}P(O)(OH)_2$, $C_{15}H_{31}P(O)(OH)_2$, $C_{16}H_{33}P(O)(OH)_2$, $C_{17}H_{35}P(O)(OH)_2$, $C_{18}H_{37}P(O)(OH)_2$, $C_6H_5P(O)(OH)_2$, $CF_3P(O)(OH)_2$, $C_2F_5P(O)(OH)_2$, $C_3F_7P(O)(OH)_2$, $C_4F_9P(O)(OH)_2$, $C_5F_{11}P(O)(OH)_2$, $C_6F_{13}P(O)(OH)_2$, $C_7F_{15}P(O)(OH)_2$, $C_8F_{17}P(O)(OH)_2$, $CF_3C_2H_4P(O)(OH)_2$, $C_2F_5C_2H_4P(O)(OH)_2$, $C_3F_7C_2H_4P(O)(OH)_2$, $C_4F_9C_2H_4P(O)(OH)_2$, $C_5F_{11}C_2H_4P(O)(OH)_2$, $C_6F_{13}C_2H_4P(O)(OH)_2$, $C_7F_{15}C_2H_4P(O)(OH)_2$, and $C_8F_{17}C_2H_4P(O)(OH)_2$, and those obtained by replacing the $-P(O)(OH)_2$ group in the above compounds by a $-P(O)(OH)OCH_3$ group, a $-P(O)(OH)OC_2H_5$ group, a $-P(O)(OCH_3)_2$ group, or a $-P(O)(OC_2H_5)_2$ group.

In order to impart better water repellency, the protective film forming agent preferably satisfies that a in the formula [2] is 1 or 2, and more preferably a is 2, i.e., the protective film forming agent is more preferably a compound represented by the following formula [3]:

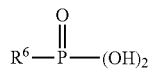

[3]

wherein $R^6$ is a C1-C18 monovalent hydrocarbon group in which part or all of the hydrogen atoms may each optionally be replaced by a fluorine atom.

In the formulas [2] and [3], $R^4$ and $R^6$ each may be an alkyl group, a phenyl group, a group obtained by replacing a hydrogen atom in the phenyl group by an alkyl group, a naphthyl group, or a group obtained by replacing part or all of the hydrogen atoms by a fluorine atom.

In order to impart better water repellency, $R^4$ and $R^6$ in the formulas [2] and [3] each preferably has a carbon number of 2 to 16, more preferably 4 to 14, particularly preferably 6 to 14. The hydrocarbon group in which part or all of the hydrogen atoms may each optionally be replaced by a fluorine atom is preferably an alkyl group, particularly preferably a linear alkyl group. If the hydrocarbon group is a linear alkyl group, the hydrophobic portion of the protective film forming agent is likely to align in the direction perpendicular to the surface of the resulting protective film, thereby improving the effect of imparting the water repellency. Thus, this configuration is more preferred. In order to impart better water repellency, $R^4$ and $R^6$ in the formulas [2] and [3] are each preferably a hydrocarbon group in which part or all of the hydrogen atoms are each replaced by a fluorine atom.

The protective film forming agent may be in the form of a salt of a compound represented by the formula [2] or [3]. Examples of the salt include ammonium salts and amine salts.

When the protective film forming chemical liquid is acidic, the water-repellent protective film forming agent contained in the protective film forming chemical liquid may be a compound represented by the following formula [4]:

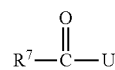

[4]

(wherein $R^7$ is a monovalent organic group having a C1-C18 hydrocarbon group or a monovalent organic group having a C1-C8 fluoroalkyl chain; U is a group selected from the group consisting of a fluoro group, a chloro group, a bromo group, and a iodo group), or the following formula [5]:

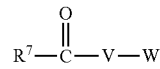

[5]

(wherein $R^8$ is a monovalent organic group having a C1-C18 hydrocarbon group or a monovalent organic group having a C1-C8 fluoroalkyl chain; V is an oxygen atom or a sulfur atom; W is a hydrogen atom or a group selected from the group consisting of alkyl groups, aromatic groups, a pyridyl group, a quinolyl group, a succinimide group, a maleimide group, a benzoxazole group, a benzothiazole group, and a benzotriazole group, where any of the hydrogen atoms in these groups may optionally be replaced by an organic group).

Examples of the compound represented by the formula 141 include $CH_3COF$, $C_2H_5COF$, $C_3H_7COF$, $C_4H_9COF$, $C_5H_{11}COF$, $C_6H_{13}COF$, $C_7H_{15}COF$, $C_8H_{17}COF$, $C_9H_{19}COF$, $C_{10}H_{21}COF$, $C_{11}H_{23}COF$, $C_{12}H_{25}COF$, $C_{13}H_{27}COF$, $C_{14}H_{29}COF$, $C_{15}H_{31}COF$, $C_{16}H_{33}COF$, $C_{17}H_{35}COF$, $C_{18}H_{37}COF$, $C_6H_5COF$, $CF_{13}COF$, $C_2F_5COF$, $C_3F_7COF$, $C_4F_9COF$, $C_5F_{11}COF$, $C_6F_{13}COF$, $C_7F_{15}COF$, $C_8F_{17}COF$, $CH_3COCl$, $C_2H_5COCl$, $C_3H_7COCl$, $C_4H_9COCl$, $C_5H_{11}COCl$, $C_6H_{13}COCl$, $C_7H_{15}COCl$, $C_8H_{17}COCl$, $C_9H_{19}COCl$, $C_{10}H_{21}COCl$, $C_{11}H_{23}COCl$, $C_{12}H_{25}COCl$, $C_{13}H_{27}COCl$, $C_{14}H_{29}COCl$, $C_{15}H_{31}COCl$, $C_{16}H_{33}COCl$, $C_{17}H_{35}COCl$, $C_{18}H_{37}COCl$, $C_6H_5COCl$, $CF_3COCl$, $C_2F_5COCl$, $C_3F_7COCl$, $C_4F_{19}COCl$, $C_5F_{11}COCl$, $C_6F_{13}COCl$, $C_7F_{15}COCl$, $C_8F_{17}COCl$, $CH_3COBr$, $C_2H_5COBr$, $C_3H_7COBr$, $C_4H_9COBr$, $C_5H_{11}COBr$, $C_6H_{13}COBr$, $C_7H_{15}COBr$, $C_8H_{17}COBr$, $C_9H_{19}COBr$, $C_{10}H_{21}COBr$, $C_{11}H_{23}COBr$, $C_{12}H_{25}COBr$, $C_{13}H_{27}COBr$, $C_{14}H_{29}COBr$, $C_{15}H_{31}COBr$, $C_{16}H_{33}COBr$, $C_{17}H_{35}COBr$, $C_{18}H_{37}COBr$, $C_6H_5COBr$, $CF_3COBr$, $C_2F_5COBr$, $C_3F_7COBr$, $C_4F_9COBr$, $C_5F_{11}COBr$, $C_6F_{13}COBr$, $C_7F_{15}COBr$, $C_8F_{17}COBr$, $CH_3COI$, $C_2H_5COI$, $C_3H_7COI$, $C_4H_9COI$, $C_5H_{11}COI$, $C_6H_{13}COI$, $C_7H_{15}COI$, $C_8H_{17}COI$, $C_9H_{19}COI$, $C_{10}H_{21}COI$, $C_{11}H_{23}COI$, $C_{12}H_{25}COI$, $C_{13}H_{27}COI$, $C_{14}H_{29}COI$, $C_{15}H_{31}COI$, $C_{16}H_{33}COI$, $C_{17}H_{35}COI$, $C_{18}H_{37}COI$, $C_6H_5COI$, $CF_3COI$, $C_2F_5COI$, $C_3F_7COI$, $C_4F_9COI$, $C_5F_{11}COI$, $C_6F_{113}COI$, $C_7F_{15}COI$, and $C_8F_{17}COI$.

Examples of the compound represented by the formula [5] include $C_5H_{11}COOH$, $C_6H_{13}COOH$, $C_7H_{15}COOH$, $C_8H_{17}COOH$, $C_9H_{19}COOH$, $C_{10}H_{21}COOH$, $C_{11}H_{23}COOH$, $C_{12}H_{25}COOH$, $C_{13}H_{27}COOH$, $C_{14}H_{29}COOH$, $C_{15}H_{31}COOH$, $C_{16}H_{33}COOH$, $C_{17}H_{35}COOH$, $C_{18}H_{37}COOH$, $C_6H_5COOH$, $C_5F_{111}COOH$, $C_6F_{13}COOH$, $C_7F_{15}COOH$, $C_8F_{117}COOH$, $C_4H_9COSH$, $C_5H_{11}COSH$, $C_6H_{13}COSH$, $C_7H_{15}COSH$, $C_8H_{17}COSH$, $C_9H_{19}COSH$, $C_{10}H_{21}COSH$, $C_{11}H_{23}COSH$, $C_{12}H_{25}COSH$, $C_{13}H_{27}COSH$, $C_{14}H_{29}COSH$, $C_{15}H_{31}COSH$, $C_{16}H_{33}COSH$, $C_{17}H_{35}COSH$, $C_{18}H_{37}COSH$, $C_6H_5COSH$, $C_4F_9COSH$, $C_5F_{11}COSH$, $C_6F_{13}COSH$, $C_7F_{15}COSH$, and $C_8F_{17}COSH$.

If the water-repellent protective film forming agent forms a salt, the protective film forming chemical liquid may contain the water-repellent protective film forming agent or a salt thereof, or a mixture thereof.

In order to impart better water repellency, the water-repellent protective film forming agent is preferably a compound represented by the formula [4] wherein $R^7$ is a monovalent organic group having a C8-C18 hydrocarbon group.

Also, in order to impart better water repellency, the water-repellent protective film forming agent is preferably a compound represented by the formula [5] wherein $R^8$ is a monovalent organic group having a C6-C18 hydrocarbon group, V is an oxygen atom, and W is a hydrogen atom.

The water-repellent protective film forming agent more preferably has a hydrophobic portion including a linear hydrocarbon group consisting of carbon and hydrogen atoms. If the linear hydrocarbon group at the hydrophobic portion consists of carbon and hydrogen atoms, the hydrophobic portion of the water-repellent protective film forming agent is likely to align in the direction perpendicular to the surface of the resulting protective film, thereby improving the effect of imparting the water repellency. Thus, this configuration is more preferred.

In consideration of the affinity with metallic substances and the effect of imparting the water repellency, particularly preferred examples of the water-repellent protective film forming agent include compounds represented by the formula [4], such as $C_8H_{17}COF$, $C_9H_{19}COF$, $C_{10}H_{21}COF$, $C_{11}H_{23}COF$, $C_{12}H_{25}COF$, $C_{13}H_{27}COF$, $C_{14}H_{29}COF$, $C_{15}H_{31}COF$, $C_{16}H_{33}COF$, $C_{17}H_{35}COF$, $C_{18}H_{37}COF$, $C_8H_{17}COCl$, $C_9H_{19}COCl$, $C_{10}H_{21}COCl$, $C_{11}H_{23}COCl$, $C_{12}H_{25}COCl$, $C_{13}H_{27}COCl$, $C_{14}H_{29}COCl$, $C_{15}H_{31}COCl$, $C_{16}H_{33}COCl$, $C_{17}H_{35}COCl$, $C_{18}H_{37}COCl$, $C_8H_{17}COBr$, $C_9H_{19}COBr$, $C_{10}H_{21}COBr$, $C_{11}H_{23}COBr$, $C_{12}H_{25}COBr$, $C_{13}H_{27}COBr$, $C_{14}H_{29}COBr$, $C_{15}H_{31}COBr$, $Cl_6H_{33}COBr$, $C_{17}H_{35}COBr$, $C_{18}H_{37}COBr$, $C_{11}H_{23}COI$, $C_{12}H_{25}COI$, $C_{13}H_{27}COI$, $C_{14}H_{29}COI$, $C_{15}H_{31}COI$, $C_{16}H_{33}COI$, $C_{17}H_{35}COI$, and $C_{18}H_{37}COI$. The above compounds are preferred because they make it easy to form a protective film on the surface of the recessed portion in a shorter time and are excellent in the effect of maintaining the water repellency in the post-cleaning step to be mentioned later.

Particularly preferred examples thereof also include compounds represented by the formula [5], such as $C_5H_{11}COOH$, $C_6H_{13}COOH$, $C_7H_{15}COOH$, $C_8H_{17}COOH$, $C_9H_{19}COOH$, $C_{10}H_{21}COOH$, $C_{11}H_{23}COOH$, $C_{12}H_{25}COOH$, $C_{13}H_{27}COOH$, $C_{14}H_{29}COOH$, $C_{15}H_{31}COOH$, $C_{16}H_{33}COOH$, $C_{17}H_{35}COOH$, $C_{18}H_{37}COOH$, $C_5H_{11}COSH$, $C_6H_{13}COSH$, $C_7H_{15}COSH$, $C_8H_{17}COSH$, $C_9H_{19}COSH$, $C_{10}H_{21}COSH$, $C_{11}H_{23}COSH$, $C_{12}H_{25}COSH$, $C_{13}H_{27}COSH$, $C_{14}H_{29}COSH$, $C_{15}H_{31}COSH$, $C_{16}H_{33}COSH$, $C_{17}H_{35}COSH$, and $C_{18}H_{37}COSH$.

When the acidic protective film forming chemical liquid contains at least one of the compounds represented by the formulas [2] to [5], the chemical liquid is likely to form an excellent water-repellent protective film on the surface of an article containing a titanium element on the surface thereof. Thus, the wafer preferably at least contains a titanium element on the surface of the recessed portion of the pattern. The chemical liquid is also likely to form an excellent water-repellent protective film on the surface of an article containing a ruthenium element on the surface thereof. Thus, the wafer may at least have a ruthenium element on the surface of the recessed portion of the pattern.

The concentration of the protective film forming agent in the protective film forming chemical liquid is preferably 0.0005 to 50% by mass in 100% by mass of the whole chemical liquid. If the concentration thereof is less than 0.0005% by mass, the effect of imparting the water repellency tends to be insufficient. If the concentration thereof exceeds 50% by mass, the agent tends to be less likely to be dissolved in an organic solvent. The concentration thereof is more preferably 0.001 to 5% by mass, particularly preferably 0.002 to 3% by mass.

The solvent to be appropriately used in the protective film forming chemical liquid is water, an organic solvent, or a liquid mixture of water and an organic solvent. Some of the water-repellent protective film forming agents may react with the solvent. Thus, the solvent is preferably appropriately selected so as not to react with the water-repellent protective film forming agent. Examples of the organic solvent to be appropriately used include hydrocarbons, esters, ethers, ketones, halogen-containing solvents, sulfoxide-type solvents, lactone-type solvents, carbonate-type solvents, alcohols, derivatives of polyhydric alcohols, nitrogen-containing solvents, and any liquid mixtures thereof.

Specific examples of the organic solvent include the same organic solvents as those to be used in the cleaning liquid A.

If part or all of the solvent(s) is/are a nonflammable one(s), preferably, the resulting protective film forming chemical liquid becomes nonflammable or the flash point thereof increase, so that the risk of the chemical liquid decreases. Many halogen-containing solvents are nonflammable, and thus nonflammable halogen-containing solvents can be suitably used as nonflammable organic solvents. Water is also suitably used as a nonflammable solvent.

From the viewpoint of the safety in terms of the Fire Service Act, the solvent is preferably a solvent having a flash point of higher than 70° C.

Based on "The Globally Harmonized System of Classification and Labelling of Chemicals" (GHS), a solvent having a flash point of not more than 93° C. is defined as a "flammable liquid". Thus, from the viewpoint of the safety, the use of a solvent having a flash point exceeding 93° C., even though it is not a nonflammable solvent, is preferred because such a solvent is likely to give a flash point exceeding 93° C. to the protective film forming chemical liquid, so that the resulting chemical liquid is less likely to be classified as a "flammable liquid".

Many of lactone-type solvents, carbonate-type solvents, alcohols having a high molecular weight or having two or more OH groups, and derivatives of polyhydric alcohols have a high flash point. Thus, in order to decrease the risk of the protective film forming chemical liquid, any of these solvents are preferably used as a solvent. From the viewpoint of the safety, it is more preferred to use, as the solvent, any of those having a flash point exceeding 70° C., specifically such as γ-butyrolactone, γ-valerolactone, γ-hexanolactone, γ-heptanolactone, γ-octanolactone, γ-nonanolactone, γ-decanolactone, γ-undecanolactone, γ-dodecanolactone, δ-valerolactone, δ-hexanolactone, δ-octanolactone, δ-nonanolactone, δ-decanolactone, δ-undecanolactone, δ-dodecanolactone, ε-hexanolactone, propylene carbonate, heptanol, octanol, ethylene glycol, diethylene glycol, 1,2-propane diol, 1,3-propane diol, dipropylene glycol, 1,2-butanediol, 1,3-butanediol, 1,4-butanediol, triethylene glycol, tripropylene glycol, tetraethylene glycol, tetrapropylene glycol, glycerin, diethylene glycol monomethyl ether, diethylene glycol monoethyl ether, diethylene glycol monopropyl ether, diethylene glycol monobutyl ether, triethylene glycol monomethyl ether, triethylene glycol monoethyl ether, triethylene glycol monopropyl ether, triethylene glycol monobutyl ether, tetraethylene glycol monomethyl ether, tetraethylene glycol monoethyl ether, tetraethylene glycol monopropyl ether, tetraethylene glycol monobutyl ether, dipropylene glycol monomethyl ether, dipropylene glycol monoethyl ether, dipropylene glycol monopropyl ether, dipropylene glycol monobutyl ether, tripropylene glycol monomethyl ether, tripropylene glycol monoethyl ether, tripropylene glycol monopropyl ether, tripropylene glycol monobutyl ether, tetrapropylene glycol monomethyl ether, ethylene glycol dibutyl ether, ethylene glycol monobutyl ether acetate, ethylene glycol diacetate, diethylene glycol ethyl methyl ether, diethylene glycol diethyl ether, diethylene glycol butyl methyl ether, diethylene glycol dibutyl ether, diethylene glycol monomethyl ether acetate, diethylene glycol monoethyl ether acetate, diethylene glycol monobutyl ether acetate, diethylene glycol diacetate, triethylene glycol dimethyl ether, triethylene glycol diethyl ether, triethylene glycol dibutyl ether, triethylene glycol butyl methyl ether, triethylene glycol monomethyl ether acetate, triethylene glycol monoethyl ether acetate, triethylene glycol monobutyl ether acetate, triethylene glycol diacetate, tetraethylene glycol dimethyl ether, tetraethylene glycol diethyl ether, tetraethylene glycol dibutyl ether, tetraethylene glycol monomethyl ether acetate, tetraethylene glycol monoethyl ether acetate, tetraethylene glycol monobutyl ether acetate, tetraethylene glycol diacetate, propylene glycol diacetate, dipropylene glycol methyl propyl ether, dipropylene glycol monomethyl ether acetate, dipropylene glycol monoethyl ether acetate, dipropylene glycol monobutyl ether acetate, dipropylene glycol diacetate, tripropylene glycol dimethyl ether, tripropylene glycol diethyl ether, tripropylene glycol dibutyl ether, tripropylene glycol monomethyl ether acetate, tripropylene glycol monoethyl ether acetate, tripropylene glycol monobutyl ether acetate, tripropylene glycol diacetate, tetrapropylene glycol dimethyl ether, tetrapropylene glycol monomethyl ether acetate, tetrapropylene glycol diacetate, butylene glycol diacetate, and glycerin triacetate. It is still more preferred to use, as the solvent, any of those having a flash point exceeding 93° C., specifically such as γ-butyrolactone, γ-hexanolactone, γ-heptanolactone, γ-octanolactone, γ-nonanolactone, γ-decanolactone, γ-undecanolactone, γ-dodecanolactone, δ-valerolactone, δ-hexanolactone, δ-octanolactone, δ-nonanolactone, δ-decanolactone, δ-undecanolactone, δ-dodecanolactone, ε-hexanolactone, propylene carbonate, ethylene glycol, diethylene glycol, 1,2-propane diol, 1,3-propane diol, dipropylene glycol, 1,2-butanediol, 1,3-butanediol, 1,4-butanediol, triethylene glycol, tripropylene glycol, tetraethylene glycol, tetrapropylene glycol, glycerin, diethylene glycol monomethyl ether, diethylene glycol monopropyl ether, diethylene glycol monobutyl ether, triethylene glycol monomethyl ether, triethylene glycol monoethyl ether, triethylene glycol monopropyl ether, triethylene glycol monobutyl ether, tetraethylene glycol monomethyl ether, tetraethylene glycol monoethyl ether, tetraethylene glycol monopropyl ether, tetraethylene glycol monobutyl ether, dipropylene glycol monopropyl ether, dipropylene glycol monobutyl ether, tripropylene glycol monomethyl ether, tripropylene glycol monoethyl ether, tripropylene glycol monopropyl ether, tripropylene glycol monobutyl ether, tetrapropylene glycol monomethyl ether, ethylene glycol diacetate, diethylene glycol butyl methyl ether, diethylene glycol dibutyl ether, diethylene glycol diacetate, diethylene glycol monomethyl ether acetate, diethylene glycol monoethyl ether acetate, diethylene glycol monobutyl ether acetate, triethylene glycol dimethyl ether, triethylene glycol diethyl ether, triethylene glycol dibutyl ether, triethylene glycol butyl methyl ether, triethylene glycol monomethyl ether acetate, triethylene glycol monoethyl ether acetate, triethylene glycol monobutyl ether acetate, triethylene glycol diacetate, tetraethylene glycol dimethyl ether, tetraethylene glycol diethyl ether, tetraethylene glycol dibutyl ether, tetraethylene glycol monomethyl ether acetate, tetraethylene glycol monoethyl ether acetate, tetraethylene glycol monobutyl ether acetate, tetraethylene glycol diacetate, propylene glycol diacetate, dipropylene glycol diacetate, dipropylene glycol monomethyl ether acetate, dipropylene glycol monoethyl ether acetate, dipropylene glycol monobutyl ether acetate, tripropylene glycol dimethyl ether, tripropylene glycol diethyl ether, tripropylene glycol dibutyl ether, tripropylene glycol monomethyl ether acetate, tripropylene glycol monoethyl ether acetate, tripropylene glycol monobutyl ether acetate, tripropylene glycol diacetate, tetrapropylene glycol dimethyl ether, tetrapropylene glycol monoethyl ether acetate, tetrapropylene glycol diacetate, butylene glycol diacetate, and glycerin triacetate.

The solvent is also preferably any of hydrocarbons, esters, ethers, ketones, lactone-type solvents, carbonate-type solvents, derivatives of polyhydric alcohols having no hydroxy group, water, and liquid mixtures thereof because they can impart better water repellency. In consideration of the replaceability by a cleaning liquid, especially an aqueous cleaning liquid, the solvent is preferably any of derivatives of polyhydric alcohols having no hydroxy group, water, and liquid mixtures thereof. In order to dissolve a large amount of the protective film forming agent, the solvent may contain an alcohol. In this case, the concentration of the alcohol is preferably 10% by mass or less, more preferably 5% by mass or less, particularly preferably 3% by mass or less, in 100% by mass of the protective film forming chemical liquid.

In order to accelerate the formation of the protective film by the protective film forming agent, the protective film forming chemical liquid may contain any additive. The amount of the additive is preferably 0.01 to 50% by mass in 100% by mass of the whole protective film forming agent.

The protective film forming chemical liquid more easily forms the protective film in a shorter time as the temperature thereof is increased. The temperature at which a uniform protective film is likely to be formed is not lower than 10° C. but lower than the boiling point of the chemical liquid. In particular, the temperature is preferably kept at not lower than 15° C. but not higher than the temperature that is 10° C. lower than the boiling point of the chemical liquid. The chemical liquid is preferably maintained at a temperature within the above range even when it is held at least in the recessed portion of the pattern. The boiling point of the chemical liquid means the boiling point of the component whose proportion by mass is the highest among the components contained in the protective film forming chemical liquid.

The protective film forming chemical liquid may be held for any period of time. The holding time is preferably 1 second to 10 minutes, more preferably 1 to 3 minutes.

The protective film forming step may be followed by replacement of the chemical liquid left at least in the recessed portion of the pattern by a cleaning liquid (hereinafter, also referred to as a "cleaning liquid B") that is different from the chemical liquid (hereinafter, this step is also referred to as a "post-cleaning step"), and then the drying step may be performed. Examples of the cleaning liquid B include aqueous cleaning liquids, organic solvents, mixtures of any aqueous cleaning liquid and any organic solvent, those obtained by mixing any of the above liquids with at least one of acids, bases, and surfactants, and any of these liquids further containing the protective film forming agent used for the protective film forming chemical liquid at a concentration lower than the chemical liquid. In order to easily remove particles and metallic impurities, the cleaning liquid B is more preferably water, an organic solvent, or a mixture of water and an organic solvent.

In the post-cleaning step, the replacement by the cleaning liquid B may be performed twice or more. In other words, the protective film forming chemical liquid may be first replaced by a first cleaning liquid B, and then the first cleaning liquid B may be successively replaced by different multiple cleaning liquids B other than the first cleaning liquid B one after another. Thereafter, the post-cleaning step may be followed by the drying step.

Examples of the organic solvent that is one preferred example of the cleaning liquid B include hydrocarbons, esters, ethers, ketones, halogen-containing solvents, sulfoxide-type solvents, alcohols, derivatives of polyhydric alcohols, and nitrogen-containing solvents.

Specific examples of the organic solvent include the same organic solvents as used for the cleaning liquid A or the protective film forming chemical liquid.

If an organic solvent is used as the cleaning liquid B, the water repellency of the resulting protective film formed on the wafer surface from the chemical liquid used in the present invention tends to be hardly deteriorated through the post-cleaning step.

FIG. 4 is a schematic view of the recessed portions 4 with a liquid being held therein and having the water repellency imparted by the protective film forming chemical liquid. The wafer illustrated in the schematic view of FIG. 4 is a part of the cross section taken along the a-a' line shown in FIG. 1. The patterned surface is covered with a protective film 10 formed from the chemical liquid, and thus has water repellency. The protective film 10 is left on the wafer surface even when the liquid 9 is removed from the pattern.

On the assumption that water is retained on the surface of the protective film 10 formed from the protective film forming chemical liquid at least on the surface of the recessed portion of the pattern of the wafer, the contact angle with water is preferably 50° to 130°. In such a case, the pattern collapse is less likely to occur. The greater the contact angle is, the better the water repellency is. Thus, the contact angle with water is still more preferably 60° to 130°, particularly preferably 65° to 130°.

Next, as described in the drying step, the liquid held in the recessed portions 4 on which the protective film is formed from the chemical liquid is removed from the pattern by drying. At this time, the liquid held in the recessed portion may be the chemical liquid used in the protective film forming step, the cleaning liquid B used in the post-cleaning step, or the liquid mixture thereof. The liquid mixture contains a protective film forming agent at a concentration lower than the protective film forming chemical liquid. The liquid mixture may be a liquid during the replacement of the chemical liquid by the cleaning liquid B or may be a liquid mixture obtained by mixing the protective film forming agent with the cleaning liquid B in advance. For good cleanliness of the wafer, the liquid is particularly preferably water, an organic solvent, or a mixture of water and an organic solvent. The previous liquid may be removed from the patterned surface and the cleaning liquid B may be then held on the patterned surface, and thereafter the drying may be performed.

If a cleaning treatment (post-cleaning step) is performed after the surface treatment with the chemical liquid, in order to easily remove particles and impurities on the patterned surface, the time of this step, i.e., the time for holding the cleaning liquid B is preferably 1 second or longer, more preferably 3 seconds or longer. In order to maintain the water repellency of the protective film formed on the patterned surface, use of an organic solvent as the cleaning liquid B tends to make it easy to maintain the water repellency of the wafer surface even after the post-cleaning. If the cleaning time is too long, the productivity may be poor. Thus, the time is preferably within 15 minutes.

In the drying step, the liquid held on the pattern is removed by drying. The drying is preferably achieved by any well-known drying technique such as spin drying, IPA (2-propanol) vapor drying, Marangoni drying, heat drying, air drying, hot air drying, or vacuum drying.

Next, a film removing step of removing the protective film 10 is preferably performed. In order to remove the water-repellent protective film, it is effective to cleave the C—C bond and/or C—F bond in the water-repellent protective film. Any method that cleaves the bond can be used. Examples thereof include light application to the wafer surface, heating of the wafer, exposure of the wafer to ozone, exposure of the wafer surface to plasma, and corona discharge on the wafer surface.

In the case of light application, removal of the protective film 10 is preferably achieved by applying ultraviolet rays including a wavelength of shorter than 340 nm and a wavelength of shorter than 240 nm, which respectively correspond to the bond energy (i.e., 83 kcal/mol) of the C—C bond and the bond energy (i.e., 116 kcal/mol) of the C—F bond in the protective film 10. Examples of the light source in this case include metal halide lamps, low pressure mercury lamps, high pressure mercury lamps, excimer lamps, and carbon arc lamps. With a metal halide lamp, for example, the UV irradiance is preferably 100 mW/cm² or higher, particularly preferably 200 mW/cm² or higher, in terms of a value measured using a radiometer (radiometer:

UM-10, Konica Minolta Sensing; light receptor: UM-360 (peak sensitive wavelength: 365 nm, measurement wavelength range: 310 to 400 nm)). If the irradiance is lower than 100 mW/cm$^2$, it may take a long time to remove the protective film 10. A low pressure mercury lamp is preferred because it emits ultraviolet rays of a shorter wavelength, so that the protective film 10 can be removed in a short time even with a low irradiance.

In the case of removing the protective film 10 by light application, it is particularly preferred to decompose the constitutional components of the protective film 10 by ultraviolet rays and to generate ozone at the same time, and to oxidation-evaporate the constitutional components of the protective film 10 by the generated ozone. This is because such a treatment can be performed in a short time. The light source in this case may be a low pressure mercury lamp or an excimer lamp. The wafer may be heated under light application.

In the case of heating the wafer, the wafer is preferably heated at 400° C. to 1000° C., more preferably 500° C. to 900° C. The heating time is preferably 10 seconds to 60 minutes, more preferably 30 seconds to 10 minutes. In this step, any of ozone exposure, plasma exposure, and corona discharge may be used in combination. The light application may be performed while heating the wafer.

Examples of the technique of removing the protective film 10 by heating include a technique of bringing the wafer into contact with a heat source and a technique of placing the wafer under a heated atmosphere, such as in a heating furnace. The technique of placing the wafer under a heated atmosphere is an industrially advantageous way because, even when multiple wafers are treated, the energy for removing the protective film 10 is easily uniformly applied to the wafer surfaces, so that the technique is easy to handle and the treatment is finished in a short time at high treatment capacity.

In the case of exposure of the wafer to ozone, it is preferred to supply the wafer surface with ozone generated by application of ultraviolet rays from a low pressure mercury lamp or by low-temperature discharge at high voltage, for example. The wafer may be irradiated with light or may be heated while exposed to ozone.

In the film removing step, the protective film on the wafer surface can be efficiently removed by combining any of the aforementioned light application, heating, ozone exposure, plasma exposure, and corona discharge.

EXAMPLES

The following will describe examples that specifically disclose the embodiments of the present invention. However, the present invention is not limited to these examples.

Formation of a pattern of recessed and projected portions on a surface of a wafer and replacement of a cleaning liquid held at least in the recessed portion of the pattern by another cleaning liquid are techniques that have been studied and have already established in other documents. Thus, the present invention evaluates a difference in the effect of imparting the water repellency among various combinations of a cleaning liquid in the pre-treating step (pre-treating step 1) and a protective film forming chemical liquid. In the examples, the cleaning liquid to be brought into contact with the wafer surface for evaluating the contact angle was water, which is a representative aqueous cleaning liquid.

In the case of a wafer having a pattern of recessed and projected portions on a surface thereof, however, the contact angle of the protective film 10 itself formed on the patterned surface cannot be exactly evaluated.

As is disclosed in JIS R3257 "Testing method of wettability of glass substrate", the contact angle with a drop of water is evaluated by dropping a several microliters of water onto a surface of a sample (substrate) and measuring the angle formed between the drop of water and the surface of the substrate. In the case of a wafer having a pattern, however, the contact angle is very large. This is due to the Wenzel effect or the Cassie effect; in other words, this is because the contact angle is affected by the surface shape (roughness) of the substrate and the apparent contact angle with a drop of water increases.

Thus, in the present examples, the chemical liquid was applied to a wafer having a smooth surface to form a protective film on the wafer surface. The resulting protective film was considered as a protective film formed on the surface of a wafer that has a pattern of recessed and projected portions formed on the surface thereof. Then, the evaluations were performed using this protective film. In the present examples, a "tungsten-film-coated wafer" (represented by W in the table) having a tungsten layer on the silicon wafer having a smooth surface and a "titanium-nitride-film-coated wafer" (represented by TiN in the table) having a titanium nitride layer on the silicon wafer having a smooth surface were each used as a wafer having a smooth surface.

The specification will be given below. The following will specifically describe the methods of evaluating the wafer supplied with the protective film forming chemical liquid, the preparation of the protective film forming chemical liquid, the pre-treatment (cleaning of wafer), the surface treatment on the wafer surface with the protective film forming chemical liquid, and the results of evaluating the wafer supplied with the protective film forming chemical liquid.

[Methods of Evaluating Wafer Supplied with Protective Film Forming Chemical Liquid]

With respect to the methods of evaluating the wafer supplied with the protective film forming chemical liquid, the following evaluations (1) to (3) were performed.

(1) Contact Angle Evaluation of Protective Film Formed on Wafer Surface

About 2 μl of pure water was dropped on the wafer surface having a protective film formed thereon, and the angle (contact angle) formed between the drop of water and the wafer surface was measured using a contact angle meter (CA-X series, Kyowa Interface Science Co., Ltd.).

(2) Removability of Protective Film

The sample was irradiated with UV light from a metal halide lamp for two hours under the following conditions, and the removability of the protective film in the film removing step was evaluated. A contact angle with the drop of water of 30° or lower after the irradiation was evaluated as acceptable.

Lamp: M015-L312 (output: 1.5 kW, Eye Graphics Co., Ltd.)

Irradiance: 128 mW/cm$^2$ (measured value under the following conditions)

Measurement device: UV radiometer (UM-10, Konica Minolta Sensing)

Light receptor: UM-360 (Detection wavelength: 310 to 400 nm, peak wavelength: 365 nm)

Measurement mode: measurement of irradiance (3) Evaluation of Surface Smoothness of Wafer after Removal of Protective Film The surface of the wafer was observed using an atomic force microscope (SPI3700, Seiko Instruments & Electronics Ltd., 2.5 μm-square scanning), and the difference ΔRa (nm) in the center-line average surface roughness Ra (nm) on the surface before and after the wafer cleaning was determined. The Ra value is a three-dimensionally expanded value obtained by applying the center-line average surface roughness defined in JIS B0601 to the measured surface, and was calculated as the "average value of the absolute values of the differences from the base surface to the specified surface" by the following formula:

$$Ra = \frac{1}{S_0} \int_{Y_T}^{Y_B} \int_{X_L}^{X_R} |F(X, Y) - Z_0| dX\, dY$$

wherein $X_L$, $X_R$, $Y_B$, and $Y_T$ each are the measurement range in the X coordinate or the Y coordinate; $S_0$ is an area on the assumption that the measured surface is an ideally flat surface and is a value of $(X_R-X_L) \times (Y_B-Y_T)$; $F(X, Y)$ is a height at a measured point $(X, Y)$; and $Z_0$ is an average height within the measured surface.

The Ra value of the wafer surface before formation of the protective film and the Ra value of the wafer surface after removal of the protective film were determined, and the cases where the difference (ΔRa) therebetween is within +1 nm were evaluated as acceptable, i.e., the wafer surface was not corroded by the cleaning and no residue of the protective film was left on the wafer surface.

Example 1

(I-1) Preparation of Protective Film Forming Chemical Liquid

Octyl amine ($C_8H_{17}NH_2$) (0.05 g) used as a water-repellent protective film forming agent and propylene glycol monomethyl ether acetate (hereinafter, referred to as "PGMEA") (99.95 g) used as a solvent were mixed and stirred for one hour. Thereby, a protective film forming chemical liquid was obtained in which the concentration (hereinafter, referred to as a "protective film forming agent concentration") of the protective film forming agent was 0.05% by mass in the whole protective film forming chemical liquid.

(I-2) Cleaning of Wafer

A smooth tungsten-film-coated wafer (a silicon wafer having a 50-nm-thick tungsten layer on a surface thereof) was immersed in 1% by mass hydrochloric acid at room temperature for one minute, and then immersed in pure water for one minute (pre-treating step 1). Then, the wafer was immersed in isopropyl alcohol (hereinafter, referred to as "iPA") for one minute (pre-treating step 2).

(I-3) Surface Treatment on Wafer Surface

The tungsten-film-coated wafer was immersed in the protective film forming chemical liquid prepared in the "(I-1) Preparation of protective film forming chemical liquid" at 20° C. for three minutes (protective film forming step). Then, the tungsten-film-coated wafer was immersed in iPA for one minute (post-cleaning step), and the tungsten-film-coated wafer was taken out of the iPA and air was sprayed thereto so that the iPA on the surface was removed (drying step).

The resulting tungsten-film-coated wafer was evaluated in accordance with the above "Methods of evaluating wafer supplied with protective film forming chemical liquid". As shown in Table 1, the contact angle after the surface treatment was 91°, which indicates an excellent effect of imparting the water repellency. The contact angle after UV irradiation was lower than 100, which indicates that the protective film was successfully removed. The ΔRa value of the wafer after UV irradiation was within ±0.5 nm. This confirms that the wafer was not corroded by the cleaning and the residue of the protective film was not left after UV irradiation.

TABLE 1

| | Protective film forming chemical liquid | | | | Pre-treatment step 1 | | Protective film forming step | |
|---|---|---|---|---|---|---|---|---|
| | Protective film forming agent | Solvent | Concentration of protective film forming agent (mass %) | Wafer | Cleaning liquid | Time (min) | Temperature (° C.) | Time (min) |
| Example 1 | $C_8H_{17}NH_2$ | PGMEA | 0.05 | W | Hydrochloric acid in water | 1 | 20 | 3 |
| Example 2 | $C_{12}H_{25}NH_2$ | PGMEA | 0.05 | W | Hydrochloric acid in water | 1 | 20 | 3 |
| Example 3 | $C_{14}H_{29}NH_2$ | PGMEA | 0.05 | W | Hydrochloric acid in water | 1 | 20 | 3 |
| Example 4 | $C_8H_{17}NH_2$ | PGMEA | 0.05 | W | Acetic acid in water | 1 | 20 | 3 |
| Example 5 | $C_8H_{17}NH_2$ | PGMEA | 0.05 | W | Hydrofluoric acid in water | 1 | 20 | 3 |
| Example 6 | $C_6F_{13}C_2H_4P(O)(OH)_2$ | PGMEA | 0.002 | TiN | Ammonia water | 1 | 20 | 1 |
| Comparative Example 1 | $C_8H_{17}NH_2$ | PGMEA | 0.05 | W | Ammonia water | 1 | 20 | 3 |
| Comparative Example 2 | $C_{12}H_{25}NH_2$ | PGMEA | 0.05 | W | Ammonia water | 1 | 20 | 3 |
| Comparative Example 3 | $C_{14}H_{29}NH_2$ | PGMEA | 0.05 | W | Ammonia water | 1 | 20 | 3 |
| Comparative Example 4 | $C_8H_{17}NH_2$ | PGMEA | 0.05 | W | NaOH in water | 1 | 20 | 3 |
| Comparative Example 5 | $C_8H_{17}NH_2$ | PGMEA | 0.05 | W | Choline in water | 1 | 20 | 3 |
| Comparative Example 6 | $C_6F_{13}C_2H_4P(O)(OH)_2$ | PGMEA | 0.002 | TiN | Hydrofluoric acid in water | 1 | 20 | 1 |

TABLE 1-continued

|  | Post-cleaning step | | Evaluation results | | | |
|---|---|---|---|---|---|---|
|  | Cleaning liquid | Time (min) | Initial contact angle (°) | Contact angle after surface treatment (°) | Protective film removability (contact angle (°)) | Surface smoothness (ΔRa (nm)) |
| Example 1 | iPA | 1 | <10 | 91 | <10 | Within ±0.5 |
| Example 2 | iPA | 1 | <10 | 96 | <10 | Within ±0.5 |
| Example 3 | iPA | 1 | <10 | 97 | <10 | Within ±0.5 |
| Example 4 | iPA | 1 | <10 | 92 | <10 | Within ±0.5 |
| Example 5 | iPA | 1 | <10 | 93 | <10 | Within ±0.5 |
| Example 6 | iPA | 1 | <10 | 116 | <10 | Within ±0.5 |
| Comparative Example 1 | iPA | 1 | <10 | 70 | <10 | Within ±0.5 |
| Comparative Example 2 | iPA | 1 | <10 | 80 | <10 | Within ±0.5 |
| Comparative Example 3 | iPA | 1 | <10 | 89 | <10 | Within ±0.5 |
| Comparative Example 4 | iPA | 1 | <10 | 67 | <10 | Within ±0.5 |
| Comparative Example 5 | iPA | 1 | <10 | 78 | <10 | Within ±0.5 |
| Comparative Example 6 | iPA | 1 | <10 | 113 | <10 | Within ±0.5 |

Examples 2 to 5, Comparative Examples 1 to 5

The cleaning and evaluation of the wafer were performed in the same manner as in Example 1 except that the type of the protective film forming agent in the protective film forming chemical liquid and the type of the cleaning liquid before immersing the wafer in pure water in the pre-treating step 1 were changed as shown in Table 1.

In Examples 1, 4, and 5 in which octyl amine, which is basic, was used as the water-repellent protective film forming agent and an acidic cleaning liquid was used in the pre-treating step, better water repellency was imparted to the wafer surface after the protective film forming step than in Comparative Examples 1, 4, and 5 in which a basic cleaning liquid was used in the pre-treating step. Also, in Example 2 in which dodecyl amine ($C_{12}H_{25}NH_2$), which is basic, was used as the protective film forming agent and an acidic cleaning liquid was used in the pre-treating step, better water repellency was imparted to the wafer surface after the protective film forming step than in Comparative Example 2 in which a basic cleaning liquid was used in the pre-treating step. Further, in Example 3 in which tetradecyl amine ($C_{14}H_{29}NH_2$), which is basic, was used as the protective film forming agent and an acidic cleaning liquid was used in the pre-treating step, better water repellency was imparted to the wafer surface after the protective film forming step than in Comparative Example 3 in which a basic cleaning liquid was used in the pre-treating step.

Example 6

(II-1) Preparation of Protective Film Forming Chemical Liquid

Perfluorohexyl ethyl phosphonate ($C_6F_{13}$—$C_2H_4$—P(O)(OH)$_2$) (0.002 g) used as a water-repellent protective film forming agent and PGMEA (99.998 g) used as a solvent were mixed and stirred for one hour. Thereby, a protective film forming chemical liquid was obtained in which the protective film forming agent concentration was 0.002% by mass.

(I-2) Cleaning of Wafer

A smooth titanium-nitride-film-coated wafer (a silicon wafer having a 50-nm-thick titanium nitride layer on a surface thereof) was immersed in 1% by mass ammonia water at room temperature for one minute, and then immersed in pure water for one minute (pre-treating step 1). Then, the wafer was immersed in iPA for one minute (pre-treating step 2).

(I-3) Surface Treatment on Wafer Surface

The titanium-nitride-film-coated wafer was immersed in the protective film forming chemical liquid prepared in the "(II-1) Preparation of protective film forming chemical liquid" at 20° C. for one minute (protective film forming step). Then, the titanium-nitride-film-coated wafer was immersed in iPA for one minute (post-cleaning step), and the titanium-nitride-film-coated wafer was taken out of the iPA and air was sprayed thereto so that the iPA on the surface was removed (drying step).

The resulting titanium-nitride-film-coated wafer was evaluated in accordance with the above "Methods of evaluating wafer supplied with protective film forming chemical liquid". As shown in Table 1, the contact angle after the surface treatment was 1160, which indicates an excellent effect of imparting the water repellency. The contact angle after UV irradiation was lower than 100, which indicates that the protective film was successfully removed. The ΔRa value of the wafer after UV irradiation was within ±0.5 nm. This confirms that the wafer was not corroded by the cleaning and the residue of the protective film was not left after UV irradiation.

Comparative Example 6

As shown in Table 1, the cleaning and evaluation of the wafer were performed in the same manner as in Example 6 except that a 1% by mass solution of hydrofluoric acid in water was used as a cleaning liquid before immersing the wafer in pure water in the pre-treating step 1.

In Example 6 in which perfluorohexyl ethyl phosphonate, which is acidic, was used as the protective film forming agent and a basic cleaning liquid was used in the pre-treating step, better water repellency was imparted to the wafer surface after the protective film forming step than in Comparative Example 6 in which an acidic cleaning liquid was used in the pre-treating step.

REFERENCE SIGNS LIST

1: wafer
2: fine pattern of recessed and projected portions on wafer surface
3: projected portion of pattern
4: recessed portion of pattern
5: width of recessed portion
6: height of projected portion
7: width of projected portion
8: protective film forming chemical liquid held in recessed portion 4
9: liquid held in recessed portion 4
10: protective film

The invention claimed is:

1. A method for cleaning a wafer that has a pattern of recessed and projected portions formed on a surface thereof and contains at least one element selected from the group consisting of titanium, tungsten, aluminum, copper, tin, tantalum, and ruthenium on a surface of a recessed portion of the pattern, the method at least comprising:
   a pre-treating step of holding a cleaning liquid at least in the recessed portion of the pattern;
   a protective film forming step of holding a protective film forming chemical liquid at least in the recessed portion of the pattern after the pre-treating step; and
   a drying step of removing the liquids from the pattern by drying,
   the protective film forming chemical liquid being a chemical liquid containing a water-repellent protective film forming agent for forming a water-repellent protective film at least on the surface of the recessed portion,
   the cleaning liquid being acidic,
   the protective film forming chemical liquid being basic, and
   the cleaning liquid having a pH of 5 or less.

2. The method for cleaning a wafer according to claim 1, wherein the water-repellent protective film forming agent contained in the protective film forming chemical liquid is at least one selected from the group consisting of compounds of the following formula [1] and salt compounds thereof:

$$R^1R^2R^3N \qquad [1]$$

wherein $R^1$ is a monovalent organic group having a $C_1$-$C_{18}$ hydrocarbon group or a monovalent organic group having a $C_1$-$C_8$ fluoroalkyl chain; $R^2$ is a hydrogen atom, a monovalent organic group having a $C_1$-$C_{18}$ hydrocarbon group, or a monovalent organic group having a $C_1$-$C_8$ fluoroalkyl chain; and $R^3$ is a hydrogen atom, a monovalent organic group having a $C_1$-$C_{18}$ hydrocarbon group, or a monovalent organic group having a $C_1$-$C_8$ fluoroalkyl chain.

3. The method for cleaning a wafer according to claim 1, wherein the wafer at least contains a tungsten element on the surface of the recessed portion of the pattern.

4. The method for cleaning a wafer according to claim 1, further comprising a film removing step of removing the protective film.

5. A method for producing a wafer comprising
   a pattern forming step of forming a pattern comprising recessed and projected portions on a surface of the wafer; and
   cleaning the wafer according to the method of claim 1.

6. The method for cleaning a wafer according to claim 1, wherein a concentration of the protective film forming agent in the protective film forming chemical liquid is 0.0005 to 50% by mass based on 100% by mass of the protective film forming chemical liquid.

7. The method for cleaning a wafer according to claim 2, wherein the water-repellent protective film forming agent has a hydrophobic portion including a linear hydrocarbon group consisting of carbon and hydrogen atoms.

8. The method for cleaning a wafer according to claim 1, wherein the acid contained in the acidic cleaning liquid comprises hydrochloric acid, nitric acid, sulfuric acid, hydrofluoric acid, or phosphoric acid.

* * * * *